United States Patent [19]

Sternlicht

[11] Patent Number: 5,522,871
[45] Date of Patent: Jun. 4, 1996

[54] APPARATUS FOR CONTROLLING THE BODY TEMPERATURE OF A PATIENT

[76] Inventor: Andrew L. Sternlicht, 355 Jerusalem Rd., Cohasset, Mass. 02025

[21] Appl. No.: 301,310

[22] Filed: Sep. 6, 1994

Related U.S. Application Data

[63] Continuation of Ser. No. 911,897, Jul. 10, 1992, abandoned.

[51] Int. Cl.⁶ ................................................. A61F 7/00
[52] U.S. Cl. .................................... 607/107; 128/849
[58] Field of Search ........................ 607/96, 98, 99, 607/104, 107, 108–112; 128/849; 165/46; 219/211

[56] References Cited

U.S. PATENT DOCUMENTS

| | | | |
|---|---|---|---|
| 1,777,982 | 10/1930 | Papp | 128/402 |
| 3,674,034 | 7/1972 | Hardy | 128/379 |
| 3,757,366 | 9/1973 | Sacher | 128/400 |
| 4,376,437 | 3/1983 | Sundheim et al. | 128/402 |
| 4,532,414 | 7/1985 | Shah et al. | 128/394 |
| 4,572,188 | 2/1986 | Augustine et al. | 128/380 |
| 4,867,230 | 9/1989 | Voss | 128/402 |
| 5,044,364 | 9/1991 | Crowther | 128/373 |
| 5,106,373 | 4/1992 | Augustine et al. | 128/400 |
| 5,300,100 | 4/1994 | Hickle et al. | 607/107 |

OTHER PUBLICATIONS

"Warm Air" (Advertisement) 1991.

*Primary Examiner*—Mark S. Graham
*Attorney, Agent, or Firm*—Laff, Whitesel, Conte & Saret, Ltd.

[57] ABSTRACT

An apparatus for controlling the body temperature of a patient, received in substantially horizontal disposition on a supporting surface, wherein the apparatus includes an air heater, at least one air hose having a plurality of side apertures therein which is positionable so that it extends along the perimeter of the body of the patient, and a surgical drape receivable over the air hose and the adjacent portion of the body of the patient. Includes the steps of assembling the air hose so that it extends along the perimeter of the body of the patient, assembling a surgical drape over the air hose and the adjacent portions of the body of the patient and supplying heated air to the air hose so that the heated air is exhausted adjacent the body of the patient.

5 Claims, 4 Drawing Sheets

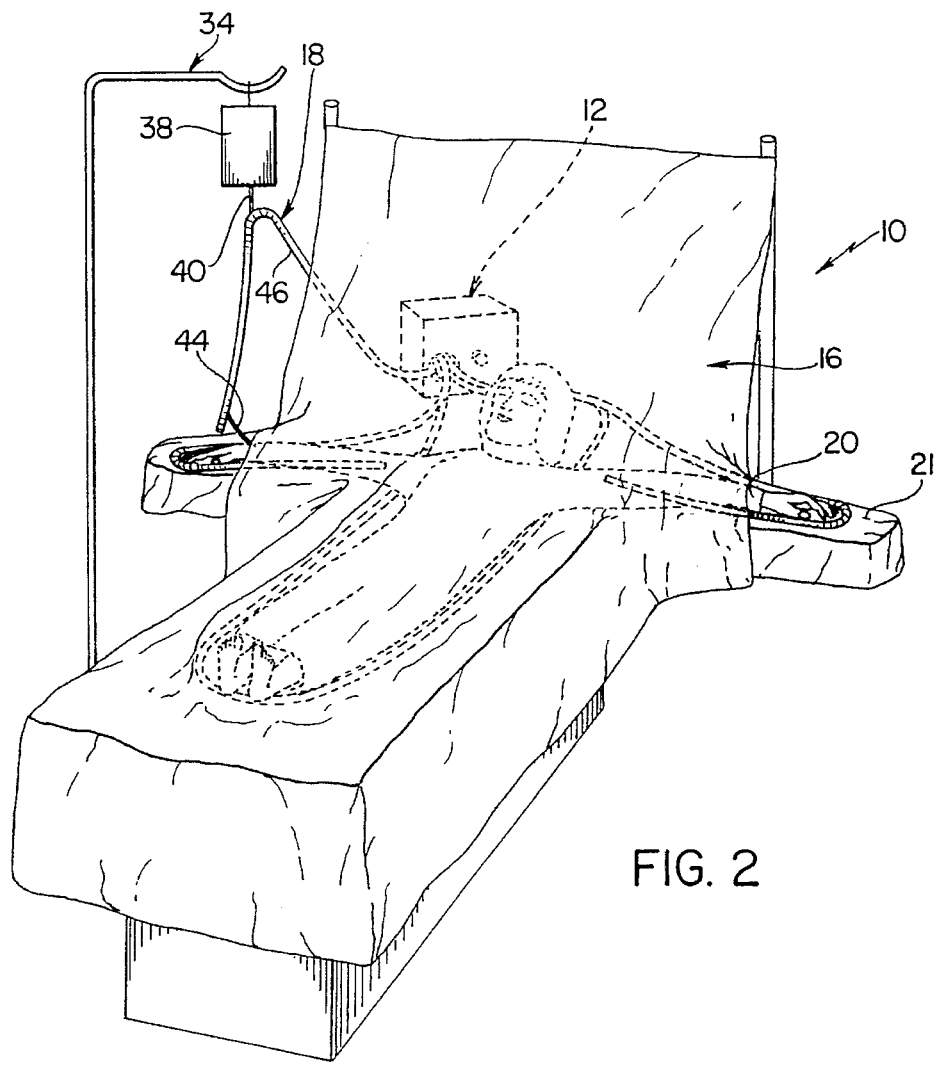
FIG. 2
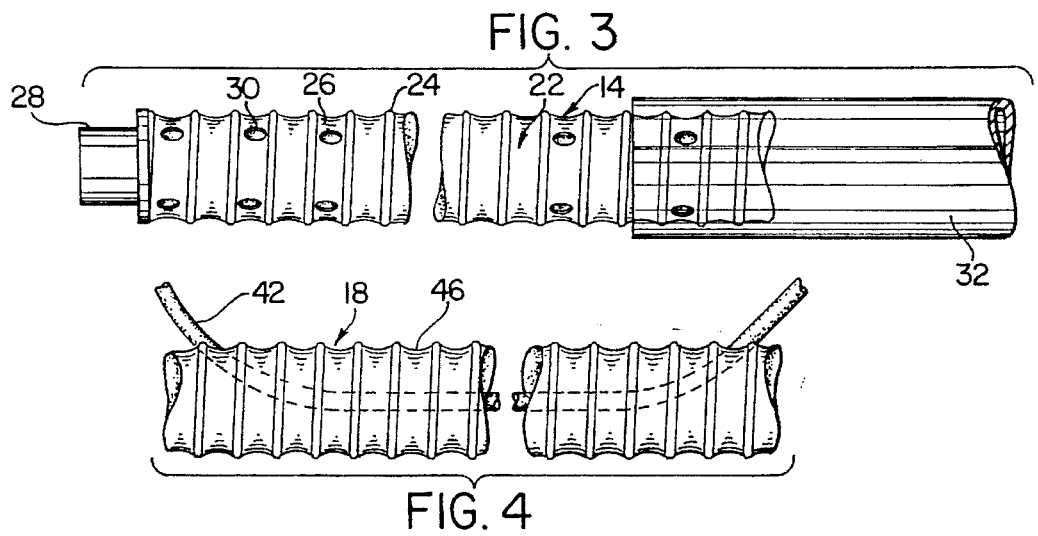
FIG. 3
FIG. 4

APPARATUS FOR CONTROLLING THE BODY TEMPERATURE OF A PATIENT

This is a continuation of application Ser. No. 07/911,897, filed Jul. 10, 1992 now abandoned.

BACKGROUND AND SUMMARY OF THE INVENTION

The instant invention relates to medical apparatus and procedures, and more particularly to a method and apparatus for controlling the body temperature of a patient.

It has been found that the body temperatures of patients are often significantly reduced during surgical procedures, particularly those which are carried out under anesthesia. This is mainly due to the side effects of most types of anesthesia, although it is also partially a result of the fact that most operating rooms are normally maintained at reduced temperature levels (between 60° F. and 65° F.) in order to prevent surgeons and other operating room personnel from becoming overly warm due to the stresses involved with most surgical procedures. It is also partially due to the fact that most patients are clothed in hospital garments which provide only minimal warmth during surgical procedures. In any event, it has been found that these factors often cooperate to lower the body temperatures of patients undergoing surgical procedures to significantly reduced levels, causing hypothermia, which can have profound deleterious effects on the cardiac, metabolic, hematological and overall physiologic well being of patients. In this regard, numerous studies have been published demonstrating the deleterious and potentially fatal effects of such post opera-tire hypothermia.

A number of apparatus have been heretofore available for controlling the body temperatures of patients during and after surgical procedures involving general anesthesia. These devices which represent the closest prior art to the subject invention of which the applicant is aware are disclosed in the HARDY U.S. Pat. No. 3,674,034; VOSS U.S. Pat. No. 4,867,230; SHAH et al, U.S. No. 4,532,414; and, AUGUSTINE et al, U.S. Pat. No. 4,572,188. Some of these previously available apparatus have included heated covers or blankets which are adapted to be received over the bodies of patients. However, it has been found that covers of this type are frequently cumbersome and impractical for use during surgical procedures. Other previously available devices have included heated pouches which are securable to various strategic areas of the bodies of patients. However, these devices have been found to be somewhat ineffective since they are only operative for heating localized areas of the bodies of patients. Still other previously available devices, such as the one disclosed in the above-mentioned U.S. patent to Shah et al, are operative for controlling the body temperatures of patients by heating IoV. fluids administered to the patients. However, many of these devices have left long sections of I.V. tubes exposed to ambient air after the fluids contained therein have been heated, so that the I.V. fluids are cooled before they reach patients. Accordingly, it has been found that there is a need for a more effective apparatus for controlling the body temperature of a patient by directly heating the body of the patient and/or more effectively heating I.V. fluids before they are administered to the patient.

The instant invention provides an effective method and apparatus for controlling the body temperature of a patient both during and after a surgical procedure, such as one involving general anesthesia. The apparatus of the instant invention comprises a heater for generating a supply of heated air and a flexible patient air hose which is operative for receiving heated air from the heater and positionable on a supporting surface so that it extends along a portion of the perimeter of the body of a patient when the patient is received in a substantially horizontal disposition on the supporting surface. The air hose has a plurality of spaced apertures in the side wall thereof, and accordingly it is operative for dispensing heated air adjacent the body of the patient. The apparatus preferably further comprises a surgical drape which is receivable over the patient air hose and the adjacent portion of the body of the patient for temporarily retaining a portion of the air dispensed from the patient air hose adjacent the patient. In one embodiment of the subject invention, the surgical drape is unattached to the air hose, whereas in a second embodiment the air hose is loosely attached to the underside of the surgical drape so that the air hose and the surgical drape can be assembled on a patient as a unit and then adjusted as needed. The patient air hose is normally constructed so that it is positionable so that it extends along substantially the entire perimeter of the body of the patient, and it preferably comprises an elongated section of corrugated air hose having sequential annular raised and recessed sections in the outer surface thereof. However, it will be understood that the hose is preferably also constructed so that it is adaptable so that it only extends along selected portions of the perimeter of the body of a patient. The apertures in the air hose are preferably located in the recessed sections thereof, and the apparatus preferably further comprises a flexible sleeve which is receivable over a portion of the patient air hose for restricting the outward flow of air from the apertures therein in selected areas, such as those areas where heated air from the air hose might interfere with an operating procedure. The apparatus preferably still further comprises an I.V. heater assembly including a section of elongated flexible I.V. air hose and an elongated section of one or more I.V. tubes received in the air hose so that the I.V. tubes coextend a distance therewith. The I.V. air hose is adapted for receiving heated air from the air heater, so that the heated air is operative for heating the I.V. tubing and an I.V. fluid received therein, whereby the I.V. fluid can be administered to the patient at an elevated temperature level (relative to ambient temperature) for further controlling the body temperature of the patient.

The method of the subject invention, which is operative for controlling the body temperature of a patient, comprises the steps of assembling the patient air hose on a supporting surface, so that the air hose extends along a portion of the perimeter of the body of the patient and feeding heated air to the interior of the air hose, so that at least a portion of the heated air is dispensed through the apertures adjacent the body of the patient. The air is preferably dispensed substantially uniformly around the body of the patient, and the method preferably further comprises applying a surgical drape over the air hose and the adjacent portion of the body of the patient, and it preferably still further comprises feeding heated air to an I.V. heater hose surrounding an I.V. tube in order to heat an I.V. fluid in the I.V. tube before the I.V. fluid is administered to the patient.

It has been found that the method and apparatus of the subject invention can be effectively utilized for controlling the body temperature of a patient both during and after a surgical procedure involving general anesthesia. In this regard, it has been found that by dispensing heated air from an air hose which is assembled so that it extends along the perimeter of the body of a patient, it is possible to effectively maintain the body temperature of the patient at a normal level, despite the effects of anesthesia. It has been further found that it is possible to even more effectively control the body temperature of a patient when a surgical drape is applied to the patient so that the surgical drape extends over the air hose and the adjacent portion of the body of the patient in order to maintain heated air which is dispensed from the air hose in close contact with the body of the patient. Even still further, it has been found that by heating an I.V. fluid which is administered to a patient by passing an I.V. tube containing the I.V. fluid through an elongated I.V. air hose which coextends a distance with the I.V. tube and which preferably terminates adjacent the patient, it is possible to effectively further control the body temperature of the patient.

Accordingly, it is a primary object of the instant invention to provide an effective apparatus for controlling the body temperature of a patient.

Another object of the instant invention is to provide an effective apparatus for controlling the body temperature of a patient by exhausting heated air along the perimeter of the body of the patient.

Another object of the instant invention is to provide an effective method for controlling the body temperature of a patient by dispensing heated air along the perimeter of the body of the patient.

An even still further object of the instant invention is to provide an effective method and apparatus for controlling the body temperature of a patient by heating an I.V. fluid before it is administered to the patient.

Other objects, features and advantages of the invention shall become apparent as the description thereof proceeds when considered in connection with the accompanying illustrative drawings.

DESCRIPTION OF THE DRAWINGS

In the drawings which illustrate the best mode presently contemplated for carrying out the present invention:

FIG. 2 is a perspective view of the apparatus of the instant invention as assembled with a patient on an operating table and including a surgical drape;

FIG. 3 is a side elevational view of a section of patient air hose;

FIG. 4 is a side elevational view of the I.V. heater assembly;

DESCRIPTION OF THE INVENTION

Figure 1:
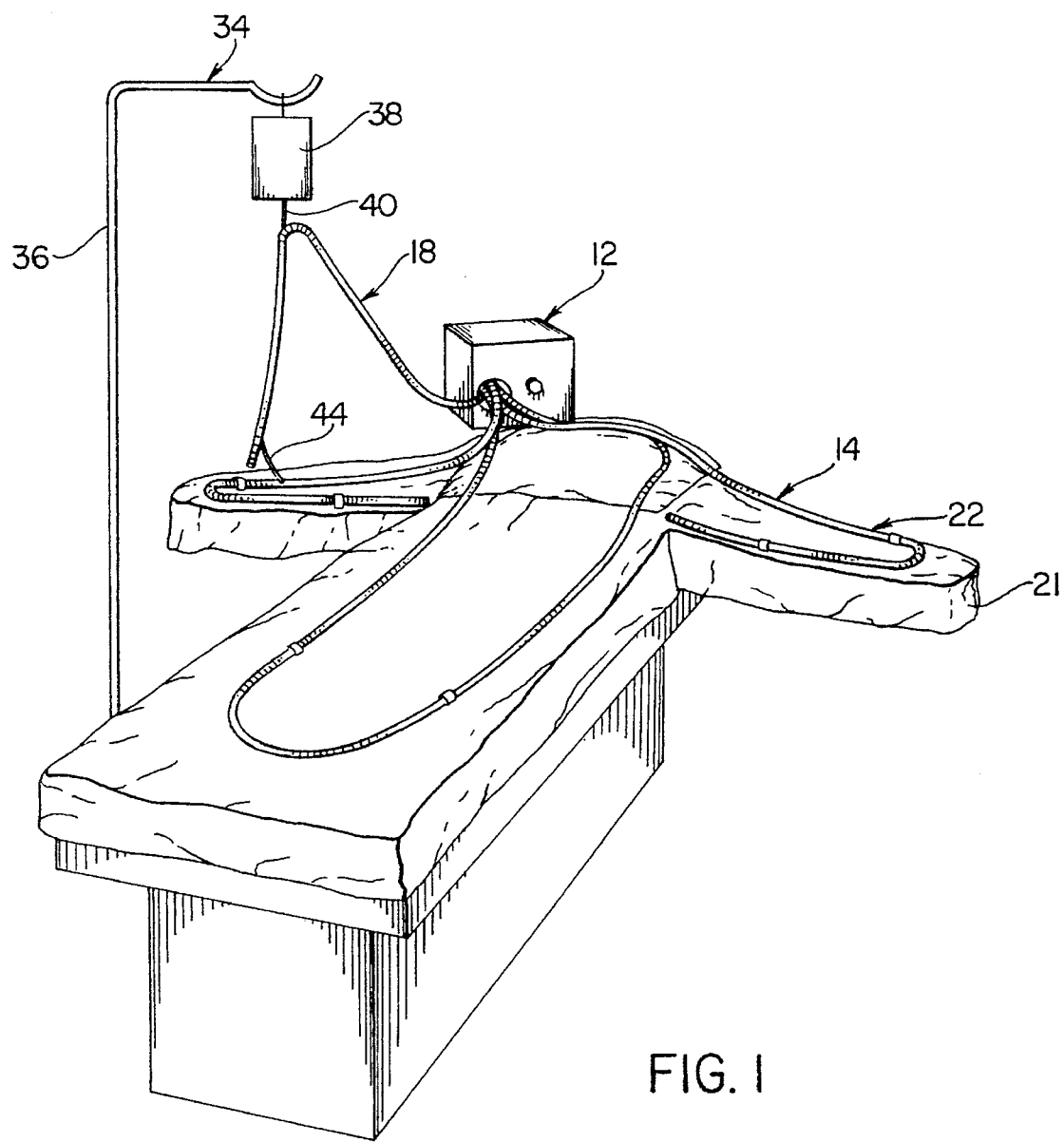
FIG. 1 is a perspective view of the apparatus of the instant invention as assembled on an operating table.

Referring now to the drawings, the apparatus for controlling the body temperature of a patient of the subject invention is illustrated in FIGS. 1 and 2 and generally indicated at 10 in FIG. 2. The apparatus 10, which can be constructed for use with adult, pediatric or neonatal patients, comprises a heater unit generally indicated at 12, a plurality of patient air hoses generally indicated at 14, a surgical drape illustrated in FIG. 2 and generally indicated at 16, and an I.V. heater assembly generally indicated at 18. During operation of the apparatus 10, the heater unit 12 is operative for supplying heated air to the patient air hoses 14, so that the air hoses 14 are operative for dispensing heated air along the perimeter of the body of a patient 20 received in a substantially horizontal disposition on a substantially horizontal surface, such as defined by an operating table 21 or a conventional hospital bed. The surgical drape 16 functions as an insulative barrier which is operative for temporarily retaining heated air dispensed through the air hoses 14 adjacent the body of the patient 20, and the I.V. heater assembly 18 is operative for heating an I.V. fluid before it is administered to the body of the patient 20 in order to further control the body temperature of the patient 20.

The heater unit 12 comprises an air heater and blower unit which is preferably electrically powered and preferably operative for generating a continuous stream of air having a temperature of between approximately 20° C. and 50° C. The heater unit 12 is preferably provided with a suitable air filter and a temperature controller having several temperature control settings for controlling the temperature of the air discharged therefrom within this range. The heater unit 12 is preferably also selectively operative for generating an unheated air stream to enable the apparatus 10 to be also utilized for supplying unheated air to patients in order to reduce the body temperatures of patients when required. In any event, the heater unit 12 is operative for supplying a sufficient quantity of air to the hoses 14 so that air from the heater unit 12 can be dispensed along substantially the entire perimeter of the body of the patient 20.

The air hoses 14 preferably comprise flexible corrugated air hose sections generally indicated at 22, which have sequential annular raised and recessed portions 24 and 26, respectively, in the outer surface thereof. As shown, an air hose section 22 is provided for warming the lower extremities, and two air hose sections are provided for warming the upper extremities. The air hose sections 22 preferably have friction fit connector tubes 28 of male and female configurations at 17 opposite ends thereof for interconnecting a plurality of the hose sections 22 as needed. Each of the hose sections 22 has a plurality of apertures 30 formed therein in the recessed areas 26 thereof for dispensing air adjacent the body of the patient 20. The air hoses 14 can alternatively be of open-ended or closed-ended construction, depending on the amount of air supplied from the heater unit 12 and the number of apertures 30 provided in the hoses 14. Further, as illustrated in FIGS. 1 and 2, the hose sections 22 can alternatively be assembled in a closed loop configuration, wherein air is supplied to opposite ends of an elongated section of connected tubes 22 by the heater unit 12 or in a free-ended configuration, wherein the terminal ends of the hoses 14 are unconnected. In any event, the important point is that the hose sections 22 are sufficiently flexible to enable them to be assembled around the perimeter of the body of the patient 20, and they are preferably reinforced to prevent them from readily collapsing. Further, the apertures 30 in the hose sections 22 are preferably located in the recessed sections 26 to prevent them from becoming obstructed when the hose sections 22 are positioned on a supporting surface, such as the operating table 21, and to normally prevent direct apposition of a patient's skin with a hose aperture. Still further, the hose sections 22 are preferably constructed so that the portions of the hose sections 22 which are furthest from the heater unit 12 have the highest number of apertures 30 therein so as to achieve an even distribution of heated air around the perimeter of a patient. The hoses 14 preferably further comprise one or more tubular sleeves 32 which are received on the hose sections 22 so that they are longitudinally positionable in different locations thereon in order to obstruct the outward flow of air from the apertures 30 in predetermined segments of the hoses 14. Accordingly, it is possible to position one of the sleeves 32 adjacent to an area such as an operating site, in order to prevent air exhausted from the apertures 30 from interfering with or contaminating a surgical procedure.

The surgical drape 16 is of conventional construction, and it is preferably applied over the patient 20 and the patient air hoses 14, so that it is operative for temporarily retaining at least a portion of the air exhausted from the air hoses 14 adjacent the body of the patient 20. It will be understood that the surgical drape 16 can be adapted to accommodate various surgical procedures and that it can be secured by suitable means to the body of the patient 20 as needed to retain it in position thereon. Further, the drape 16 preferably has an adhesive backing for securing it to a patient at an operative window site in order to further prevent the apparatus 10 from interfering with an operative procedure.

Figure 7:
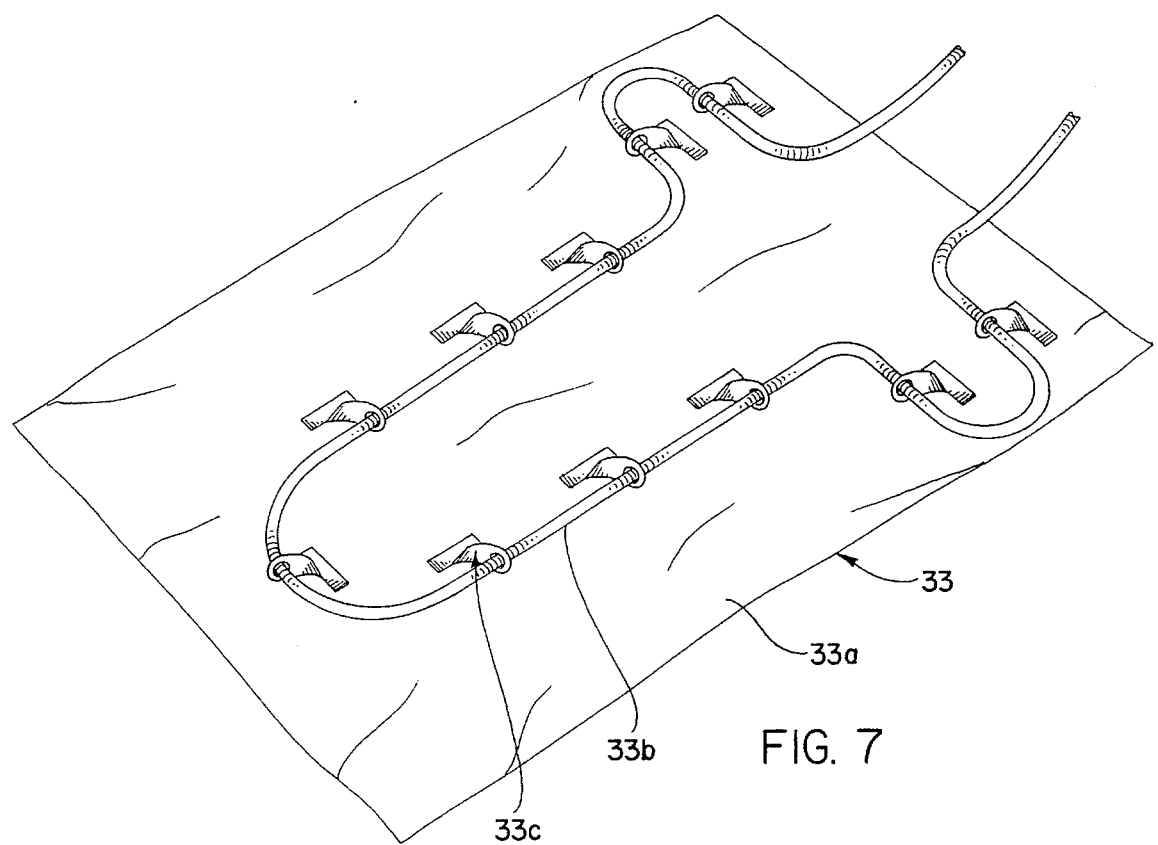
FIG. 7 is a bottom perspective view of a second embodiment of the air hose and surgical drape portions of the apparatus of the instant invention.
Figure 8:
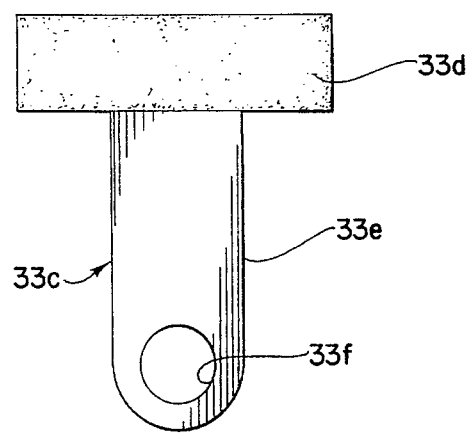
FIG. 8 is a plan view of one of the hose attachment members thereof in a flattened disposition.

A second embodiment of the heater hose and surgical drape portions of the apparatus of the subject invention is illustrated in FIGS. 7 and 8, and generally indicated at 33 in FIG. 7. The apparatus 33 comprises a surgical drape 33a, an air hose assembly 33b, and a plurality of flexible attachment members 33c which are operative for loosely attaching the air hose 33b to the underside of the surgical drape 33a. As illustrated in FIG. 8, each of the attachment members 33c includes a base portion 33d which is permanently attached to the surgical drape 33a, such as by a suitable adhesive, and an elongated tab portion 33e having an aperture 33f therein. The air hose 33b extends through the apertures 33f and the attachment members 33c, and the attachment members 33c are preferably secured to the underside of the surgical drape 33a so that they are operative for loosely retaining the air hose 33b in a configuration which corresponds generally to the configuration of the perimeter of a patient. However, since the attachment members 33c include the flexible leg portions 33e, and since the air hose 33b passes loosely through the apertures 33f, the air hose 33b can nevertheless be readily adjusted and repositioned as needed to accommodate patients of various different sizes. Further, it will be understood that the apparatus 33 can be alternatively constructed in various different embodiments which are adapted for applying heated air to various selected portions of the bodies of patients which, for example, may not include the arms of patients. In any event, because the air hose 33b is attached to the underside of the surgical drape 33a, the apparatus 33 can be laid directly onto the body of a patient as a unit, and the air hose 33b can thereafter be repositioned as necessary to achieve the desired heating effects. The air hose 33b is generally similar in construction to the air hoses 14, and it has a plurality of apertures therein which are operative for distributing air along the perimeter of the body of a patient. Further, because the air hose 33b is attached to the underside of the surgical drape 33a, the apparatus 10 is positionable over the body of a patient so that the surgical drape 33a is operative for temporarily retaining a portion of the air exhausted from the air hose 33b in the proximity of the patient. Hence, the air exhausted from the air hose 33b can be effectively utilized for both directly heating the body of the patient and for heating adjacent bedding on which the patient is supported.

The I.V. heater unit 18 is adapted to be utilized in combination with a conventional I.V. apparatus 34, including an I.V. stand 36, an I.V. fluid container 38, and an I.V. tube 40. As illustrated in FIG. 4, the I.V. heater 18 comprises an elongated section of I.V. tubing 42 which is adapted to be connected to the I.V. tubing 40 for receiving an I.V. fluid therefrom. The I.V. tubing 42 is further adapted to be connected to a patient connector assembly 44 for administering the I.V. fluid to the patient 20. The I.V. heater unit 18 further comprises an I.V. heater hose 46 which is preferably also of corrugated reinforced construction, and which surrounds and coextends a distance with the I.V. tube 42, preferably terminating adjacent the patient connector assembly 44. The hose 46 is adapted to be connected to the heater unit 12 for receiving heated air therefrom. Accordingly, the I.V. heater unit 18 is operative for heating an I.V. fluid passing through the I.V. tube 42, so that the fluid is heated before it is administered to the patient 20. Further, because the heater air hose 46 preferably terminates adjacent to the body of the patient 20, the I.V. fluid does not normally pass through a sufficient length of I.V. tubing after it leaves the hose 46 to allow the I.V. fluid to become cooled before it is administered to the patient 20. Accordingly, the patient heater unit 18 is also operative for effectively controlling the body temperature of the patient 20 by heating an I.V. fluid immediately before the fluid is administered to the patient 20.

Figure 5:
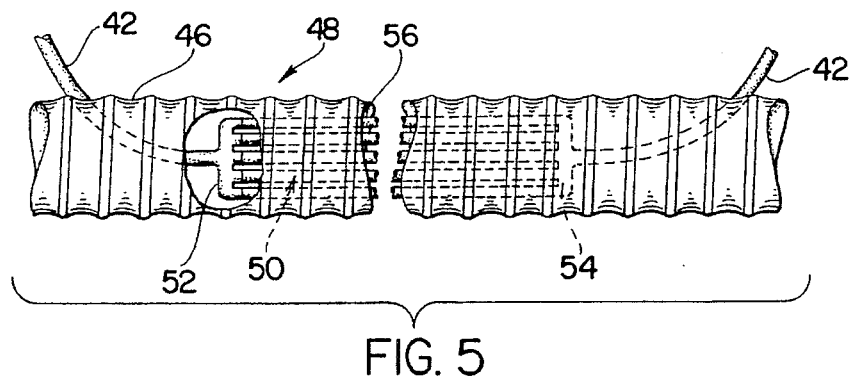
FIG. 5 is a side elevational view of a second embodiment of the I.V. heater assembly.

Referring now to FIG. 5, a second embodiment of the I.V. heating apparatus of the subject invention is illustrated and generally indicated at 48. The heating apparatus 48 comprises an air hose 46, an I.V. tube 42, and a heat exchanger assembly generally indicated at 50 comprising inlet and outlet manifolds 52 and 54, respectively, and a plurality of tubes 56 which extend between the inlet and outlet manifolds 52 and 54, respectively. The heat exchanger assembly 50 is disposed in the interior of the air hose 46, and it is interposed in an intermediate location in the longitudinal extent of the I.V. tubing 42. Accordingly, an I.V. fluid entering the air hose 46 through the I.V. tubing 42 passes into the inlet manifold 52 and then into the heating tubes 56, which provide additional surface area and residence time for heating the I.V. fluid in the air hose 46. The I.V. fluid from the heating tubes 56 then passes into the outlet manifold 54 and out through the terminal section of the I.V. tube 42, which is preferably connected to a patient connector assembly 44. Accordingly, the I.V. heater unit 48 is operative for more efficiently heating an I.V. fluid passing through the I.V. tube 42 before the I.V. fluid reaches a patient.

Figure 6:
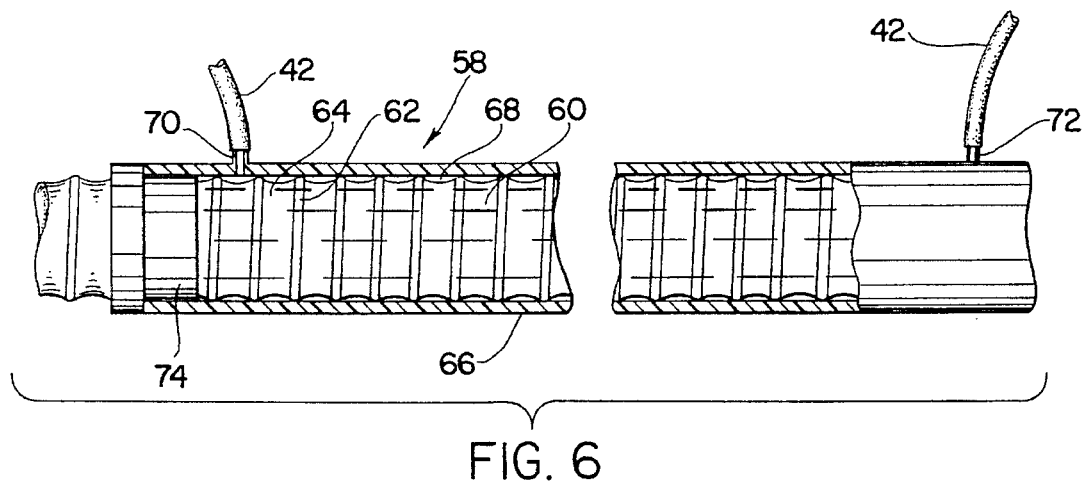
FIG. 6 is a side elevational view of a third embodiment of the I.V. heater assembly.

A third embodiment of the I.V. heater of the subject invention is illustrated in FIG. 6 and generally indicated at 58. The I.V. heater 58 comprises a section of reinforced flexible air hose 60, which is configured so that the outer surface thereof is defined by a continuous helix with raised and recessed sections 62 and 64, respectively. The heater unit 58 further comprises an outer sleeve 66, which is received on the air hose 60 so that the sleeve 66 is received in sealed engagement with the raised helical sections 62. As a result, a continuous helical channel 68 is formed between the recessed sections 64 and the sleeve 66. The I.V. heater 58 still further comprises inlet and outlet tubes 70 and 72, and a pair of end plugs 74 which seal the ends of the channel 68. The inlet and outlet tubes 70 and 72 are positioned so that they communicate directly with the channel 68 so that the inlet tube 70 can be utilized for introducing an I.V. fluid into the channel 68, and so that the outlet tubing 72 can be utilized for passing an I.V. fluid outwardly from the channel 68 into the outlet portion of the I.V. tubing 42. Accordingly, an I.V. fluid entering the channel 68 from the inlet tube 70 passes in a helical flow pattern around the perimeter of the air hose 60 so that the I.V. fluid is heated by air passing through the hose 60 by the time it reaches the outlet tube 72. Consequently, it is seen that the I.V. heater 58 is operative for heating an I.V. fluid by contacting it with the outside surface of the air hose 60 rather than passing the I.V. fluid through one or more tubes in the interior of the air hose 60.

Accordingly, for use of the apparatus 10 in accordance with the method of the instant invention, the patient air hoses 14 are assembled on a supporting surface, such as the operating table 21, so that the air hoses 14 extend along substantially the entire perimeter of the body of the patient 20. Thereafter, the heater unit 12 is operative for supplying heated air to the air hoses 14 so that the air is dispensed adjacent the perimeter of the body of the patient 20. Further, the surgical drape 16 is preferably assembled over the body of the patient 20 so that it also extends over the air hoses 14 to maintain a portion of the air dispensed from the air hoses 14 in intimate contact with the body of the patient 20. Alternatively, the apparatus 33 can be assembled as a unit on the body of the patient 20 so that the air hose 33b extends around the perimeter of the patient's body and so that air exhausted from the air hose 33b is maintained with the patient 20. Further, an I.V. fluid administered to the patient 20 is passed through the I.V. tube 42 which extends through the air hose 46, so that the I.V. fluid is heated by the air passing through the air hose 46 before it is administered to the patient. Alternatively, the I.V. fluid can be heated utilizing one of the I.V. heaters 48 or 58.

It is seen therefore that the instant invention provides an effective method and apparatus for controlling the body temperature of a patient. The apparatus 10 is operative for dispensing heated air along the perimeter of the body of the patient and for temporarily maintaining at least a portion of the heated air in intimate contact with the patient's body. The I.V. heater units 18, 48 and 58 are operative for heating I.V. fluids before they enter the patient's body in a manner which prevents the I.V. fluids from becoming cooled before they enter the patient's body. Accordingly, it is seen that the method and apparatus of the subject invention represents significant advancements in the medical art which have substantial commercial merit.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. An apparatus for controlling the body temperature of a patient, the body of the patient having a perimeter as defined by an outline of the patient to include upper extremities, and lower extremities, the apparatus comprising:

a) heater means for generating a supply heated air;

b) flexible patient air hose means for receiving heated air from the heater means, the patient air hose means being directly positionable so that the patient air hose means extends along a portion of the perimeter of the body of the patient;

c) the patient air hose means further having a plurality of side apertures therein for dispensing the heated air immediately adjacent the portion of the body of the patient in a manner which enables at least a portion of the heated air to transfer heat to the portion of the body of the patient after passing through the side apertures;

d) the air hose means having a section of flexible hosing for warming the lower extremities of the patient, the section of flexible hosing being configurable for conforming along the perimeter of the lower extremities for providing a flow of heated air the lower extremities;

e) two sections of flexible hosing for warming the upper extremities of the patient;

f) the two sections of flexible hosing being configurable for conforming along the perimeter of the upper extremities for providing a flow of heated air over the upper extremities, one of the two sections for warming one arm of the patient and the other of the two sections for warming the other arm of the patient;

g) surgical drape means paying an upper side and an opposite under side separate from the hose means;

h) the surgical drape means including a drape receivable over the portion of the body of the patient and over the patient air hose means when the air hose means is positioned so as to extend along a portion of the perimeter of the body of the patient, the drape temporarily retaining a portion of the air dispensed from the patient air hose means adjacent the patient for keeping the portion of the body of the patient warm; and i) means loosely pre-attaching the air hose means to the underside of the surgical drape in a predetermined configuration.

2. The apparatus of claim 1, said means loosely pre-attaching said air hose means attaching said air hose means to said drape in a configuration corresponding generally to an outline of a human figure.

3. The apparatus of claim 1, said means loosely attaching said air hose means comprising a plurality of flexible tabs on said drape, said tabs having apertures therein, said hose passing through said apertures.

4. The apparatus of claim 1, said patient air hose means comprising an elongated section of corrugated air hose having sequential annular raised and recessed sections in the outer surface thereof, said apertures being disposed in said recessed sections.

5. The apparatus of claim 1 further comprising a flexible tubular sleeve of only slightly greater diameter than said air hose means receivable over a portion of said patient air hose means for restricting the outward flow of air from the apertures therein.

* * * * *

UNITED STATES PATENT AND TRADEMARK OFFICE
CERTIFICATE OF CORRECTION

PATENT NO. : 5,522,871
DATED : June 4, 1996
INVENTOR(S) : Andrew L. Sternlicht

It is certified that error appears in the above-indentified patent and that said Letters Patent is hereby corrected as shown below: On the title page, item [57], line 8, after <u>and the adjacent portion of the body of the patient.</u>, delete "Includes the steps of assembling the air hose so that it extends along the perimeter of the body of the patient, assembling a surgical drape over the air hose and the adjacent portions of the body of the patient and supplying heated air to the air hose so that the heated air is exhausted adjacent the body of the patient."

In column 1, line 55, after <u>by heating</u>, and before <u>fluids</u>, delete "IoV." and substitute therefor --I.V.--.

In column 4, line 42, after <u>at</u>, and before <u>opposite ends</u>, delete "17".

In column 7, line 54, after <u>upper extremities</u>, and before <u>and</u>, delete ",".

In column 8, line 15, after <u>heated air</u>, and before <u>the lower</u>, insert --over--.

In column 8, line 25, after <u>drape means</u>, and before <u>an upper side</u>, delete "paying" and substitute therefor --having--.

Signed and Sealed this

Twenty-ninth Day of October 1996

*Attest:*

BRUCE LEHMAN

*Attesting Officer*  *Commissioner of Patents and Trademarks*